United States Patent [19]

Dawe

[11] 4,432,761
[45] Feb. 21, 1984

[54] VOLUMETRIC DROP DETECTOR

[75] Inventor: Garfield A. Dawe, Lindenhurst, Ill.

[73] Assignee: Abbott Laboratories, North Chicago, Ill.

[21] Appl. No.: 423,369

[22] Filed: Sep. 24, 1982

Related U.S. Application Data

[63] Continuation of Ser. No. 276,119, Jun. 22, 1981, abandoned.

[51] Int. Cl.³ ............................ A61M 5/00; G01F 1/00
[52] U.S. Cl. ................................. 604/253; 73/861.41; 73/55; 222/420; 250/560
[58] Field of Search ................... 604/253, 251, 65, 50; 73/861.41, 861, 55; 250/560, 561; 222/420, 422

[56] References Cited

U.S. PATENT DOCUMENTS

| | | | |
|---|---|---|---|
| 2,880,764 | 4/1959 | Pelavin | 141/130 |
| 3,226,137 | 7/1974 | Clarke | 73/194 |
| 3,500,366 | 3/1970 | Chesney et al. | 340/222 |
| 3,563,090 | 2/1971 | Deltour | 73/194 |
| 3,815,414 | 6/1974 | Hellstrom | 73/861.41 |
| 3,898,637 | 8/1975 | Wolstenholme | 34/239 |
| 4,038,982 | 8/1977 | Burke et al. | 128/DIG. 13 |
| 4,088,411 | 5/1978 | Ahlquist et al. | 250/560 X |
| 4,152,767 | 5/1979 | Laliotos | 250/560 X |
| 4,314,484 | 2/1982 | Bowman | 73/861.41 |

Primary Examiner—Stephen C. Pellegrino
Attorney, Agent, or Firm—Neil E. Hamilton

[57] ABSTRACT

A device for measuring the volume of flow in a liquid conveying apparatus wherein the length and velocity of a liquid column are measured. Drops of the liquid are formed and directed into a length of measurement tubing having a known internal diameter. As the liquid column is passed through the measurement tubing its length is determined by two spaced apart liquid sensors. The actual length is determined by calculating the time elapsed for the leading edge of the liquid column to interrupt the two liquid sensors. The time for the trailing edge to pass the first sensor is proportioned to the length of the column and the quotient of the two values will give the actual length. Accordingly, accurate volume determinations can be made irrespective of velocity change such as due to viscosity, surface tension or back pressure. The device of this invention is especially adapted to be used in conjunction with an intravenous administration set.

19 Claims, 4 Drawing Figures

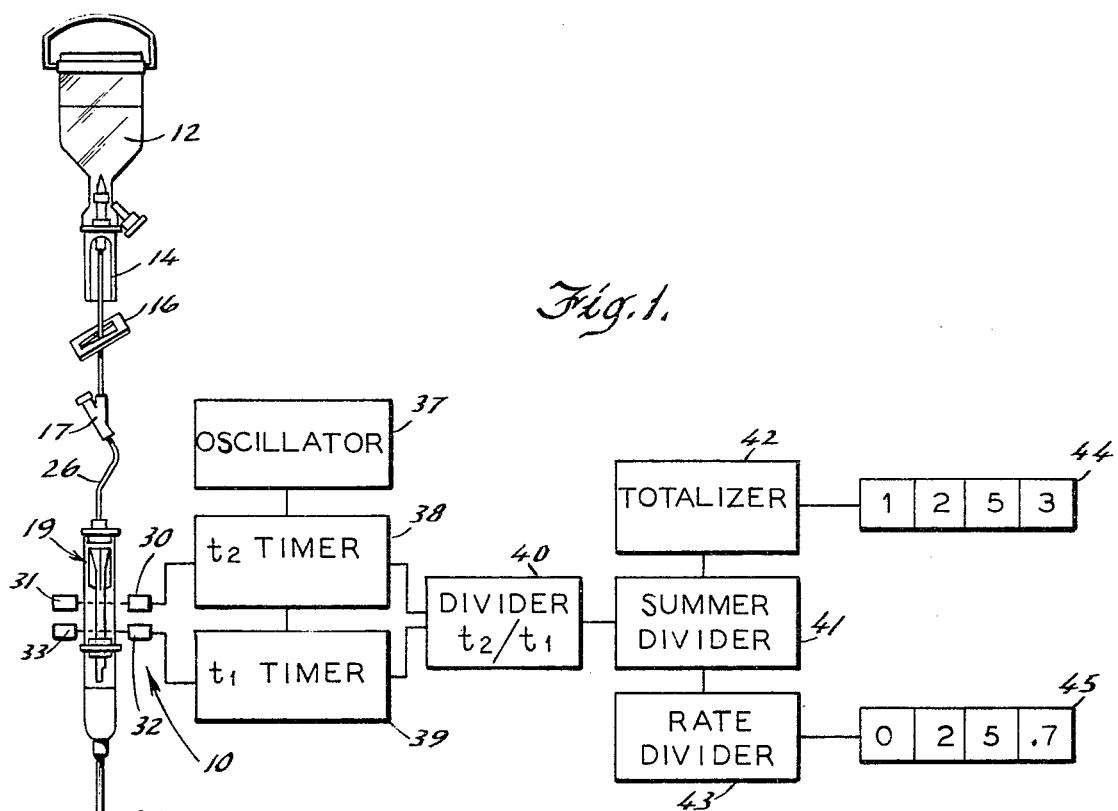
Fig. 1.
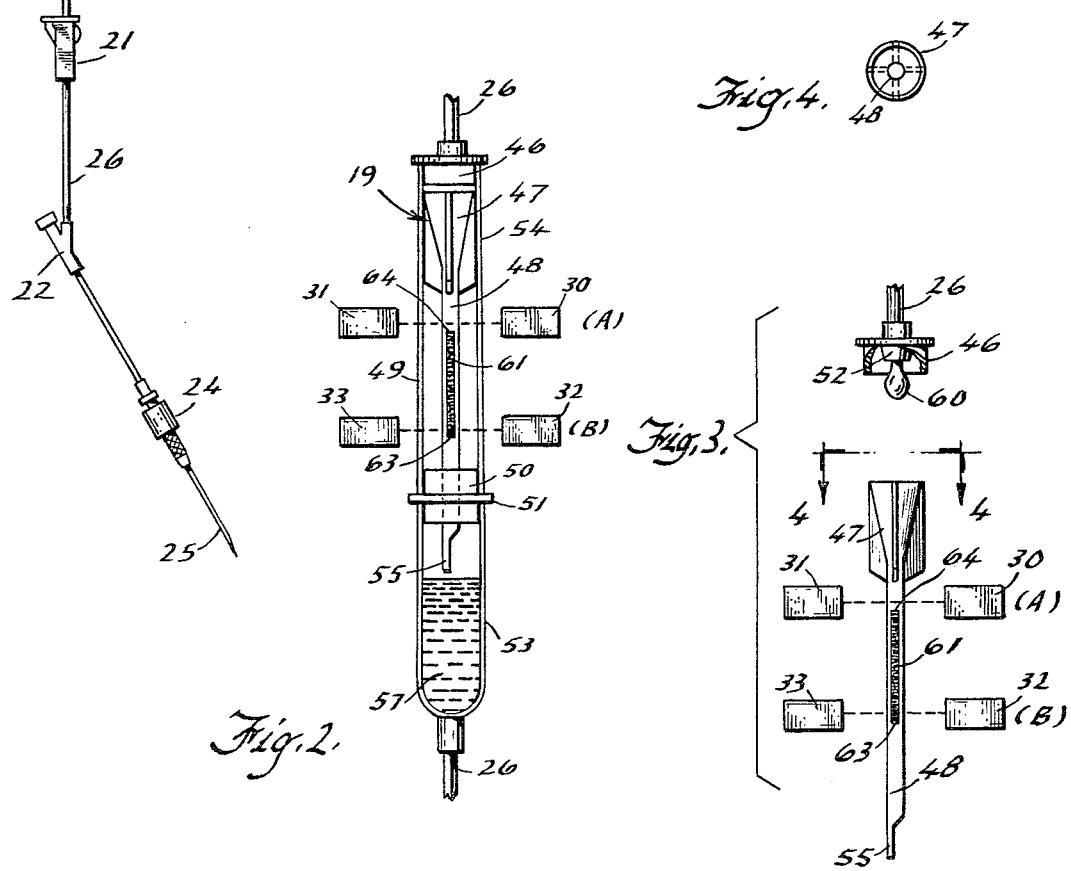
Fig. 2.
Fig. 3.
Fig. 4.

VOLUMETRIC DROP DETECTOR

This is a continuation of application Ser. No. 276,119, filed June 22, 1981 now abandoned.

BACKGROUND OF THE INVENTION

This invention relates to an apparatus for monitoring the rate of liquid flow in a liquid conveying apparatus. More particularly, this invention relates to an apparatus for measuring the drop volume of a liquid in an I.V. administration set by utilizing a section of relatively narrow tubing into which the drops are directed and the length of the drop is optically and electronically measured by passage past two spaced apart liquid sensors.

A drop volume measuring apparatus is described in U.S. Pat. No. 2,880,764 wherein two light sources are employed to measure the volume of a falling drop. Two beams of light are utilized in U.S. Pat. No. 3,563,090 for liquid drop monitoring and a single capacitive detector with two electrodes is described in U.S. Pat. No. 3,500,366. In U.S. Pat. No. 3,826,137, an apparatus is described for measuring liquid flow which employs a capillary tube into which a liquid flows from a nozzle forming a stream of drops. The drops then freely fall from a nozzle where they are counted prior to falling into the capillary tube. By placing the nozzle in such a manner that the drops contact the surface of the liquid in the tubing, a drop forming gap is provided which is stated to afford accurate determination of the drop count. As there is no detection means associated with the particular drop forming mechanism, this must be done manually. In U.S. Pat. No. 3,898,637, a detection means for gas entering a human blood system from extracorporeal, tubing is described. In this particular unit, electronic detection means is afforded and placed in conjunction with a controlled restriction for the purpose of air bubble detection.

The prior art does not provide an accurate method of measuring the volume of liquid in an I.V. administration set wherein the velocity of liquid in a column is measured by means of two spaced apart liquid sensors. The prior art is either concerned with methods of forming or measuring drops of liquid, or with an electronic detection means used to restrict bubbles in a bubble detection system.

It is an advantage of the present invention to provide a means of monitoring I.V. medication by liquid column measurement which actually measures the length and velocity of flow of the liquid column. Other advantages are a volumetric drop measuring flow meter which is easily adapted to I.V. administration apparatus; can be utilized in conjunction with the usual I.V. administration drip chamber; can be manufactured in such a manner that the disposable portion is relatively inexpensive; and lends itself to be easily integrated with various electronic functions.

SUMMARY OF THE INVENTION

The foregoing advantages are accomplished and the shortcomings of the prior art are overcome by the improved volumetric measuring device disclosed, wherein a liquid drop forming means is utilized in conjunction with a length of measurement tubing having a known internal diameter to form a liquid column. First and second liquid sensor means are positioned with respect to the measurement tubing. Electronic means are operatively connected to the first and second liquid sensors to measure the velocity and length of the liquid column as it passes through the measurement tubing. Collecting means are disposed with respect to the measurement tubing to receive the measured drops. Tube connector means are provided in conjunction with the drop forming means and the collecting means for connection with first and second lengths of flexible tubing normally associated with an I.V. administration set. In order to direct the liquid drops from the drop forming means into the measurement tubing, a funnel member is provided, forming an upper extending portion of the measurement tubing. The first and second liquid sensors are preferably photodetectors of the phototransistor type which are operatively connected to two electronic timing mechanisms as well as an oscillator. A divider is electrically connected to the two timing mechanisms and in turn to a summer divider. A totalizer is operatively attached to the summer divider which can render a digital reading of the volume delivered. If desired, a rate divider can be interconnected to the summer divider to give a digital reading of the delivery rate.

BRIEF DESCRIPTION OF THE DRAWINGS

A better understanding of the volumetric drop detector of this invention will be accomplished by reference to the drawings wherein:

FIG. 1 is a view in side elevation of the volumetric measuring device shown in conjunction with a standard I.V. administration set and indicating the sensors and electronic components in schematic form.

FIG. 2 is an enlarged view of the measurement tubing for the drops and showing it combined with a fluid chamber.

FIG. 3 is a view in side elevation showing the drop measurement tubing with a funnel portion in conjunction with the drop forming member and illustrating the form of the drop as it passes through the measurement tubing.

FIG. 4 is a view in horizontal section taken along line 4—4 of FIG. 3.

DESCRIPTION OF THE PREFERRED EMBODIMENT

Proceeding to a detailed description of the preferred embodiment of the present invention, the volumetric drop detector 10 is shown for use in conjunction with a standard parenteral administration unit composed of a solution container 12, the contents of which are connected by and made accessible through a vented piercing pin 14. The usual length of tubing 26 extends from vented piercing pin 14 to a drop forming and measurement means 19. The standard Y-reseal injection site is afforded at 17 and the flow of fluid to the drop forming measurement means can be terminated by slide clamp 16. Extending from the opposing end of drop forming and measurement means 19 is a similar length of flexible tubing 26 to which is attached a standard roller flow control clamp 21 with another Y-injection site 22 disposed between needle adapter 24 with hypodermic needle 25 and the clamp 21.

The volumetric drop detector 10 includes liquid drop forming and measurement means 19 as well as two pairs of oppositely positioned, light sources 31 and 33 and photodetectors 30 and 32 serve as liquid sensors. Photodetector 30 is interconnected to a timer 38 and photodetector 32 is attached to timer 39. The signals from timer 38 are expressed in digital format developed by the oscillator 37. A divider 40 is fed signals from timers 38 and 39 while a summer divider 41 receives signals from divider 40 which in turn is connected to a totalizer 42. A digital display unit 44 is provided to give a digital readout from the totalizer. Also interconnected to the summer divider 41 is a rate divider 43 which also has a digital delivery rate display 45 operatively connected to it.

Referring to FIG. 2, it will be seen that the drop forming and measurement means 19 includes measurement tubing 48 having a funnel portion 47 at one end and a discharge tip 55 at the other. A drop forming or drip means 46 also serves as a connecting means for tubing 26 at the upper end as well as an annular, fluid-tight attachment for tubing housing 49. A centering sleeve 50 for tubing 48 also serves as an attachment for chamber 53 to which is secured a second length of tubing 26. Chamber 53 serves as a collecting means for I.V. solution 57 whereas funnel portion 47 in conjunction with drop forming means 46 will serve as a drip chamber 54.

FIG. 3 illustrates the formation of a drop of liquid 60 from drop forming means 46 which will be effected through the drop forming nozzle 52 axially aligned with respect to funnel portion 47 of measurement tubing 48. The numeral 61 shows an elongated liquid drop as it would be formed due to the internal diameter of measurement tubing 48. Preferably, this section of tubing is formed from a nonwetting plastic material and preferably polypropylene so as to present a nonwetting surface for the liquid. The preferred internal diameter is approximately 2.28 mm and the preferred length is 6 cm.

OPERATION

A better understanding of the advantages of the volumetric measuring device of this invention will be had by a description of its operation. It should be pointed out that a key factor in the operation of the volumetric measuring is in knowing the internal diameter of measurement tubing 48. Once this is established, a standard unit of volume can be obtained by measuring the length of the drop. The drop forming and measuring means 19 which will have the measurement tubing 48 contained therein, will be supplied as a component in the usual I.V. administration set. This will include a vented piercing pin 14, a slide clamp 16, as well as a Y reseal injection site 17. When it is desired to administer the contents of solution container 12, the vented piercing pin will be placed in fluid communication with the contents of container 12 and liquid will flow through tubing 26 and to drop forming means 46. A drop forming and measurement means 19 will have been placed and secured between oppositely positioned pairs of light sources and photodetectors 30, 31 and 32, 33 so that they are aligned in a parallel manner with measurement tubing 48. In this instance, the preferred photodetectors are of the opto-electronic type and are phototransistors. Selection of a normal drop length can be made such that the controlled inside diameter of the drop measuring tube 48 will give a standard unit of volume. For example, a drop length of 1.62 cm. in a tube with a 0.114 cm radius will equal a volume of 0.067 cc or 1/15th cc.

A volumetric drop measuring flowmeter device is described in copending U.S. Ser. No. 423,370 filed 09/24/80 by the same inventor. Reference is made to the method of detecting or measuring the length of the liquid column produced by the drop as it passes through tube 48. Although the optical array, capacitance, optical shadow and other similar methods are feasible for measuring the liquid column, they all make instantaneous length measurements. Analysis of these methods has pointed out disadvantages of each in terms of component cost, complexity of design, and operating range. The latter in particular, is demonstrated by the problem of how to measure the longest possible liquid column. For example, a one inch long optical array could not correctly measure a 1¼ inch column; similarly, capacitor plates could be exceeded (assuming that the preferred length would be less than the longest column). Only the time-of-flight method can accept columns of any length, but in its conventional form it requires a constant velocity and tests have indicated that the velocity changes widely with various solution viscosities. Efforts to compensate for the velocity change in the time-of-flight method, have thus brought about the development of a unique solution.

A liquid column such as column (61) formed by a drop 60 as it falls through a tube of known inside diameter can be measured in length by determining the time it takes for the column to pass a photodetector such as 30. The velocity must be known, so that the length can be calculated as the product of the velocity and time:

$$L = Vt$$

In a system where velocity can change (with viscosity, surface tension and back pressure), the velocity can be measured at the same time by using a second photodetector 32 at a known distance from the first 30, 31.

The leading edge 63 of liquid column 61 will interrupt photodetector 30 (A) and then photodetector 32, 33 (B) with the time elapsed between as a measure of the velocity. The time for the trailing edge 64 to pass photodetector A is proportional to the length of the column and the quotient of the two values will give the actual length. For example, if the velocity for a column of water is 200 mm/sec and the time from A to B is 0.1 sec:

$$L = 200 \times 0.1 = 20 \text{ mm}$$

A similar column of viscous solution might have a velocity of 100 mm/sec and require 0.2 sec.

$$L = 100 \times 0.2 = 20 \text{ mm}$$

The output signals from the photodetector start at the same time; for a long column:

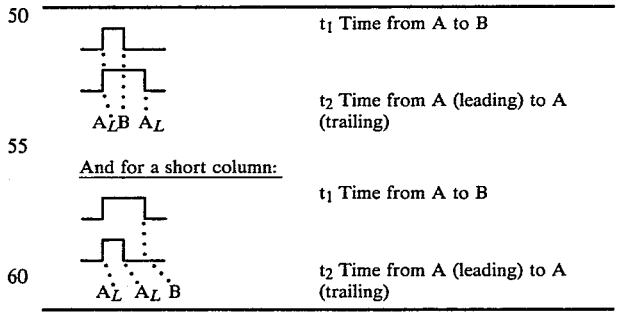

| | |
|---|---|
| | $t_1$ Time from A to B |
| | $t_2$ Time from A (leading) to A (trailing) |
| And for a short column: | |
| | $t_1$ Time from A to B |
| | $t_2$ Time from A (leading) to A (trailing) |

If D is the distance from photodetector A to photodetector B and $t_1$ is the time required for the leading edge of a liquid column to travel from A to B then velocity is $$V = D/t_1$$

Similarly, if L is the length of the liquid column and $t_2$ is the time required for the column to travel past photodetector A then velocity is $$V = L/t_2$$

If we assume the velocity is constant over a time interval equal to the greater of $t_1$ to $t_2$ then, $$D/t_1 = L/t_2 \text{ or } \boxed{t_2/t_1 = L/D}$$

and the ratio of the length to the known distance is the same as the ratio of the time signals.

If the time signals are converted to digital counts by gating a clock frequency into two counters for intervals $t_1$ and $t_2$ respectively, then the counts for the two signals can easily be divided to give the L to D ratio.

For example:

$t_1$ ||||||||||||| = 15 counts $t_2$ ||||||||||||||||||||||| = 26 counts then $$\frac{L}{D} = \frac{26}{15} = 1.73 \text{ or } L = 1.73 \, D$$

so the length of the column of liquid is 1.73 times as long as the distance D between the photodetectors.

The method is independent of velocity and clock frequency, provided they remain constant during the time of measurement. Also the effect of velocity change (if it should occur) is reduced, if distance A to B is selected as the typical column length, i.e., 1/15th ml if a 15 drop orifice 52 is used.

It will be appreciated that the foregoing measurements will be effected by use of the electronic components set forth in FIG. 1 with the $t_1$ function being effected by timer 39 and the $t_2$ function by timer 38. The oscillator 37 will provide the digital counting for timers 38 and 39 with the dividing function being effected by divider 40. Finally the divided signals are again divided by summer divider 41 and displayed on counter 44 as the total volume in ml by means of totalizer 42. They are also sampled for a period of time by rate divider 43 to give the rate of delivery as indicated at 45.

It will be appreciated that the monitoring or controlling of I.V. medication by drop rate methods has always been limited by the variability of drop size. Viscosity, surface tension, rate of growth and other factors spread the range of drop volumes well over plus or minus 30%. The volumetric drop detector, as disclosed herein, measures the drop volume by a unique method of capturing the fluid of a given drop inside a section of tubing which has a known cross-section and then determining its length by measuring its velocity as well as the time for the trailing edge of a liquid column to pass a given reference point.

It should be understood that while in the foregoing description certain functional circuit modules are indicated in block diagrams, microprocessor technology could readily be adapted for purposes of calculating the velocity and length of the drops as well as indicating delivery rate and volume delivered. Further, while the volumetric measuring device has been disclosed for use in an I.V. administration set, it will be appreciated that the flow meter is readily adaptable outside the medical field and could be utilized to accurately monitor or control liquid flow where an inexpensive disposable element can be advantageously utilized such as in any liquid conveying apparatus.

In the foregoing description, the measuring tubing 48 was described as being composed of a polypropylene resin material. If desired, other materials which would provide a nonwetting surface and can be formed with a small bore diameter, could be substituted, such as Teflon or glass. Further, while the diameter of tubing 48 was indicated as being 2.28 mm. in inside diameter, this diameter could range from 1 mm. to 5 mm. While the preferred length of tubing 48 is 60 mm., this could vary from 5 mm. to 130 mm. Similarly, other industrial applications especially those of highly viscous materials may utilize larger drop volumes and consequently larger diameter conduit.

It will thus be recognized that there is now provided a volumetric measuring flow meter which can accurately determine the volume of a liquid by utilizing standard electronic components in conjunction with a length of tubing having a known internal diameter. The unit can be provided so that the measuring tubing and its housing are disposable, which will lend itself to use in a disposable I.V. administration apparatus. The volumetric drop detector can be used outside the medical field, such as in any apparatus where precise volumetric flow detection is desired.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:

1. A volumetric measuring device for use with a liquid conveying apparatus including the usual first and second flow paths comprising:
   liquid drop forming means;
   a length of measurement tubing having a known internal diameter;
   means operatively associated with said drop forming means to direct liquid drops into said measurement tubing to form a liquid column;
   first and second liquid sensor means operatively positioned with respect to said measurement tubing;
   electronic means operatively associated with said first and second liquid sensor means to measure the velocity and length of said liquid column;
   collecting means positioned from said measurement tubing to receive said measured drops; and
   connector means operatively associated with said drop forming means and said collecting means for connection with said first and second flow paths.

2. The volumetric measuring device as defined in claim 1 wherein said first and second liquid sensor means are of the optoelectronic type.

3. The volumetric measuring device as defined in claim 2 wherein said electronic means includes timing means to measure the leading edge of said drop twice and trailing edge once.

4. The volumetric measuring device as defined in claim 1 wherein said means to direct liquid drops into said measurement tubing is defined by a funnel portion connected to said measurement tubing.

5. The volumetric measuring device as defined in claim 4 wherein said collecting means is defined by a chamber and said measurement tubing provides a drop discharging means at the end thereof.

6. The volumetric measuring device as defined in claim 5 further including a tubular housing member positioned to surround said measurement tubing and said funnel member, said tubular housing in fluid tight engagement with said collecting means at one end and said connector means for said drop forming means at the other, said drop forming means and said tubular housing defining a drip chamber.

7. The volumetric measuring device as defined in claim 6 wherein said collecting means is defined by a chamber member further including a centering sleeve operatively contacting said measurement tubing and said tubular housing as well as said chamber member.

8. The volumetric measuring device as defined in claim 6 further including a liquid container connection means secured to said first flow path opposite said drip chamber and an intravenous delivery device secured to said second flow path opposite said chamber member.

9. A volumetric measuring device for use with an intravenous administration apparatus including the usual first and second lengths of flexible tubing comprising:
   liquid drop forming means;
   a length of measurement tubing having a known internal diameter;
   means operatively associated with said drop forming means to direct liquid drops into said measurement tubing to form a liquid column;
   first and second liquid sensor means including two pairs of operatively positioned drop length sensors operatively positioned with respect to said measurement tubing;
   electronic means operatively associated with said first and second liquid sensor means to measure the velocity and length of said liquid column;
   collecting means positioned from said measurement tubing to receive said measured drops; and
   tubing connector means operatively associated with said drop forming means and said collecting means for connection with said first and second lengths of flexible tubing.

10. The volumetric measuring device as defined in claim 9 wherein said optoelectronic means further includes:
   a first timer;
   a second timer;
   an oscillator;
   a divider for said first and second timer;
   a summer divider; and
   a totalizer;
   said timers, oscillator, dividers and totalizer all operatively connected to provide a digital readout of the total volume delivered of said liquid columns.

11. The volumetric measuring device as defined in claim 10 further including a rate divider operatively connected to said summer divider to provide a digital readout of the delivery rate.

12. The volumetric measuring device as defined in claim 11 wherein said measurement tubing is composed of a polypropylene resin material.

13. The volumetric measuring device as defined in claim 12 wherein said measurement tubing has an internal diameter in the range of about 1 mm to about 5 mm.

14. A disposable device for monitoring or controlling liquid flow having first and second flow paths, said device for use with an optoelectronic device having at least two spaced apart electronic means to determine the length of a drop of liquid flowing therein comprising:
   liquid forming means;
   a length of measurement tubing having a known internal diameter and a length of sufficient dimension to accommodate said electronic means when positioned in oppositely disposed pairs;
   means operatively associated with said drop forming means to direct liquid drops into said measurement tubing;
   collecting means positioned from said measurement tubing to receive said measured drops; and
   connector means operatively associated with said drop forming means and said collecting means for connection with said first and second flow paths.

15. The disposable device as defined in claim 14 wherein said means to direct liquid drops into said measurement tubing is defined by a funnel portion connected to said measurement tubing.

16. The disposable device as defined in claim 15 wherein said disposable device forms a part of a disposable I.V. administration set and said collecting means is defined by a chamber and said measurement tubing provides a drop discharging means at the end thereof.

17. The disposable I.V. administration set as defined in claim 16 further including a tubular housing member positioned to surround said measurement tubing and said funnel member, said tubular housing in fluid tight engagement with said collecting means at one end and said connector means for said drop forming means at the other, said drop forming means and said tubular housing defining a drip chamber.

18. The disposable I.V. administration set as defined in claim 17 wherein said collecting means is defined by a chamber member and further including a centering sleeve operatively contacting said measurement tubing and said tubular housing as well as said chamber member.

19. The disposable I.V. administration set as defined in claim 18 further including a liquid container connection means secured to said first flow path opposite said drip chamber and an intravenous delivery device secured to said second flow path opposite said collecting means.

* * * * *

UNITED STATES PATENT AND TRADEMARK OFFICE
CERTIFICATE OF CORRECTION

PATENT NO. : 4,432,761

DATED : February 21, 1984

INVENTOR(S) : Garfield A. Dawe

It is certified that error appears in the above—identified patent and that said Letters Patent is hereby corrected as shown below:

Column 8, Claim 19, line 2 should read:

in claim 17 further including a liquid container connec-

Signed and Sealed this

Nineteenth Day of June 1984

[SEAL]

Attest:

GERALD J. MOSSINGHOFF

Attesting Officer

Commissioner of Patents and Trademarks